United States Patent
Taniguchi et al.

(10) Patent No.: US 6,228,866 B1
(45) Date of Patent: *May 8, 2001

(54) CONDENSED PIPERIDINE COMPOUND

(75) Inventors: Naoyuki Taniguchi; Kaoru Kobayashi; Masao Naka, all of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/524,255

(22) Filed: Mar. 13, 2000

Related U.S. Application Data

(63) Continuation of application No. 09/056,867, filed on Apr. 8, 1998, now Pat. No. 6,110,930.

(30) Foreign Application Priority Data

Apr. 10, 1997 (JP) .................................................. 9-91830
Oct. 7, 1997 (JP) ................................................. 9-273196

(51) Int. Cl.[7] ..................... A61K 31/435; A61K 31/438; C07D 221/04
(52) U.S. Cl. ........................... 514/299; 514/278; 546/16; 546/112
(58) Field of Search ...................... 546/16, 112; 574/278, 574/299

(56) References Cited

U.S. PATENT DOCUMENTS 5,629,322 * 5/1997 Guthikonda ........................ 514/313

FOREIGN PATENT DOCUMENTS

| WO 95/11231 | 4/1995 | (WO) . |
| WO 96/14842 | 5/1996 | (WO) . |
| WO 96/14844 | 5/1996 | (WO) . |
| WO 96/35677 | 11/1996 | (WO) . |

OTHER PUBLICATIONS

Michael I. Bukrinsky et al., "Regulation of Nitric Oxide Synthase Activity in Human Immunodeficiency Virus Type 1 (HIV–1)–infected Monocytes: Implications for HIV–associated Neurological Disease", J. Exp. Med., The Rockefeller University Press, 0022–1007/95/02/0735/11, vol. 161, Feb. 1995 pp. 735–745.

Prasad Koka, et al., "Human Immunodeficiency Virus 1–Envelop Proteins Induce Interleukin 1, Tumor Necrosis Factor α, and Nitric Oxide in Glial Cultures Derived from Fetal, neonatal, and Adult Human Brain" J. Exp. Med., The Rockefeller University Press, 0022–1007/95/10/941/11, vol. 182, Oct. 1995 pp. 941–952.

Marie-Annette Dorheim, et al. "Nitric Oxide Synthase Activity is Elevated in Brain Microvessels in Alzheimer's Disease" Biochemical and Biophysical Research Communications, pp. 659–665, vol. 205, No. 1, Nov. 30, 1994.

McCann SM, Licino J., et al., "The nitric oxide hypothesis of aging" Exp. Garontol 1998, Nov.–Dec., 333 (7–8): 813–26.

Webber et al. "Substituted 2–Iminopiperidines as Inhibitors of Human Nitric Oxide Synthase" The Journal of Medicinal Chemistry 1998, vol. 41, No. 1 96–101.

Perera DM et al., "Nitric Oxide Synthase inhibitor NG–monomethyl–L–arginine preserves sperm motility after swim–up" Fertile Steril 1996 Nov. 66 (5):830–3.

Nobunaga T., et al. "Elevated nitric oxide concentration in the seminal plasma of infertile males: nitric oxide inhibits sperm motility," Am J. Reprod Immunol 1996 Oct. 36(4):193–7.

Ding, et al. "Release of Reactive Nitrogen Intermediates and Reactive Oxygen Intermediates from Mouse Peritoneal Macrophages," J.Immunol. vol. 141: 2407–12, 1988.

Rosselli M., et al. "Effects of nitric oxide on human spermatozoa: evidence that nitric oxide decreases sperm motility and induces sperm toxicity" Hum Reprod 1995 Jul; 19(7): 1786–90.

* cited by examiner

*Primary Examiner*—Evelyn Mei Huang
(74) *Attorney, Agent, or Firm*—Sughrue, Mion, Zinn, Macpeak & Seas, PLLC

(57) ABSTRACT

A compound represented by formula (I):

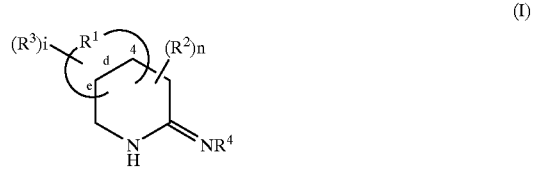

wherein all symbols are defined in the specification, or an acid addition salt thereof or a hydrate thereof; a process for preparing the same; and a nitrogen monoxide synthase inhibitor comprising the same as an active ingredient.

2 Claims, No Drawings

CONDENSED PIPERIDINE COMPOUND

This is a continuation of application Ser. No. 09/056,867 filed Apr. 8, 1998, U.S. Pat. No. 6,110,930 the disclosure of which is incorporated herein by reference.

FIELD OF THE INVENTION

This invention relates to a nitrogen monoxide synthase inhibitor. More particularly, it relates to a condensed piperidine compound represented by formula (I):

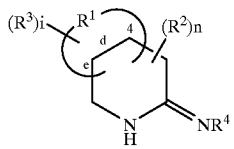

wherein all the symbols have the same meanings as defined below, or an acid addition salt or a hydrate thereof.

BACKGROUND OF THE INVENTION

The discovery that microphages, one kind of immunocompetent cells, produce a large quantity of nitrates led to the discovery that nitrogen monoxide (NO) is biologically synthesized (*Proc. Natl. Acad. Sci., U.S.A.,* Vol. 82, pp. 7738–7742 (1985) and *J. Immunol.,* Vol. 138, pp. 550–565 (1987)). In the field of circulatory organs, a substance having a relaxing action that is released from endothelial cells was discovered and named an endothelial cell-derived relaxing factor (EDRF). It was found later that the substance of EDRF is NO (*Nature,* Vol. 327, pp. 524–526 (1987)).

NO, which has recently been revealed to be produced biologically, is synthesized through the following route by the action of a nitrogen monoxide synthase (hereinafter abbreviated as NOS) on an L-arginine substrate.

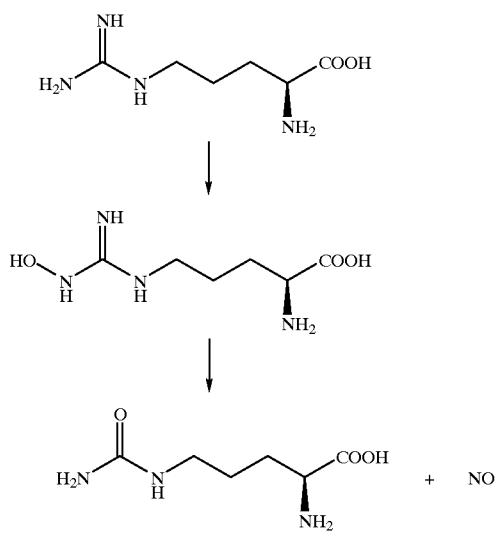

NOS includes at least a constitutive isozyme (endothelial type and neuronal type) and an inducible isozyme. Endothelial NOS exists chiefly in endothelial cells, and its activity is controlled by an intercellular calcium concentration. Neuronal NOS exists in central nervous cells, peripheral nervous cells, islet β cells, gastrointestinal nerves, the medulla of the suprarenal glands, renal macula densa, etc., and its activity is under control by an intercellular calcium concentration similarly to the endothelial type NOS.

The constitutive NOS (inclusive of endothelial type and neuronal type, hereinafter abbreviated as c-NOS) always exist in the cells in amounts almost unchangeable under physiological conditions. On the other hand, the inducible NOS (hereinafter abbreviated as i-NOS) can exist in hepatocytes, neutrophil leucocytes, macrophages, smooth muscle, fibroblasts, mesangium cells, gastrointestinal eliphelium, islet β cells, vascular smooth muscle cells, gliocytes, etc. Usually, the inducible NOS is not observed in cells but induced on stimulation by endotoxins and/or various cytokines.

NO synthesized by the action of NOS exhibits a wide variety of actions, for example, vascular relaxation, inhibition on blood platelet aggregation and adherence, inhibition on leucocyte adherence and migration, inhibition on sympathetic activity, endotoxin shocks, endotoxin- or cytokine-induced hypotension, action as a neurotransmitter, ischemic cerebral cell disturbances, antitumor action, bactericidal action, induction of autoimmune diseases, insulin dependent diabetes mellitus or arthritis, induction of post-transplantation tissue disturbances and graft rejection, and the like.

An NO synthase inhibitor (NOS inhibitor) is not only useful in analyzing the in vivo physiological activities of NO but is expected as a therapeutic agent for shocks or ischemic diseases. Therefore, various NOS inhibitors have recently been developed.

For example, arginine analogues, such as Nω-monomethyl-L-arginine (L-NMMA), Nω-nitro-L-arginine (L-NNA), Nω-amino-L-arginine (L-NAA), and Nω-iminoethylornithine (L-NIO), are known as a substrate competitive agent. Known cofactor competitive inhibitors include diphenylene iodonium (DPI), di-2-thienyl iodonium (DTI), and calcineurin. Known gene transcription induction inhibitors include corticosteroid, TGFβ, IL-4 and IL-10.

WO 96/35677 discloses that a compound represented by formula (A) shown below, a salt thereof, and a pharmaceutically acceptable ester thereof are a nitrogen monoxide synthase inhibitor:

(A)

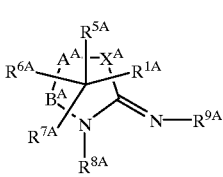

wherein $R^{1A}$ is selected from hydrogen, lower alkyl, lower alkenyl, lower alkynyl, alkyloxy, thioalkoxy, cycloalkyl, heterocyclyl, and aryl, which may optionally be substituted by lower alkyl, lower alkenyl, lower alkynyl, cycloalkyl, heterocyclyl, aryl, hydroxy, lower alkoxy, aryloxy, thiol, lower thioalkoxy, halogen, cyano, nitro, amino, alkylamino, dialkylamino, aminoalkyl, dialkylaminoalkyl, arylamino, aminoaryl, alkylaminoaryl, acylamino, carboxy, carboxyalkyl, $CONR^{10A}R^{11A}$, $S(O)R^{10A}$, $S(O)_2R^{10A}$, $SO_2NR^{10A}R^{11A}$, $PO(OR^{10A})(OR^{11A})$ amidino, guanidino; wherein all said substitutions may be optionally substituted with one or more of the following: halogen, lower alkyl, amino, alkylamino, dialkylamino, aminoalkyl, aminoacyl, carboxyl, carboalkoxy, carboaryloxy, carboalkylaryloxy, hydroxy, lower alkoxy, S(O)R$^{10A}$, S(O)$_2$R$^{10A}$, amidino, guanidino;

X$^A$=NR$^{2A}$, O, S, SO, SO$_2$, (CH$_2$)$_{pA}$, CH=CH;

pA=0 to 6;

A$^A$=NR$^{3A}$, O, S, SO, SO$_2$, (CH$_2$)$_{qA}$, CH=CH;

q$^A$=0 to 6;

B$^A$=NR$^{4A}$, O, S, SO, SO$_2$, (CH$_2$)$_{vA}$ or CH=CH;

v$^A$=0 to 6;

R$^{2A}$=hydrogen, lower alkyl, aryl, heterocyclyl;

R$^{3A}$=hydrogen, lower alkyl, aryl, heterocyclyl;

R$^{4A}$=hydrogen, lower alkyl, aryl, heterocyclyl;

R$^{5A}$, R$^{6A}$ and R$^{7A}$ are independently selected from hydrogen, lower alkyl, lower alkenyl, lower alkynyl, heterocyclyl, hydroxy, lower alkoxy, thiol, lower thioalkoxy, S(O)R$^{9A}$, S(O)$_2$R$^{9A}$, halogen, nitro, amino, alkylamino, dialkylamino, aminoalkyl, dialkylaminoalkyl, arylamino, aminoaryl, alkylaminoaryl, acylamino, carboxyl, carboalkoxy, carboaryloxy, carboarylalkyloxy, cyano, aminocarbonylalkoxy, aminocarbonylamino, aminocarbonylaminoalkyl, haloalkyl, SO$_2$NR$^{10A}$R$^{11A}$, wherein all said substitutions may be optionally substituted with one or more of the following: lower alkyl, amino, alkylamino, dialkylamino, aminoalkyl, aminoacyl, carboxyl, carboalkoxy, carboaryloxy, carboalkylaryloxy, hydroxy, lower alkoxy;

R$^{5A}$ and R$^{6A}$ may be optionally taken together to form an alicyclic, heterocarbon, heterocyclic or aromatic hydrocarbon and said optionally formed ring may be optionally substituted with one or more of the following: lower alkyl, lower alkenyl, lower alkynyl which may be optionally substituted with carboxyl, carboalkoxy, carboaryloxy, carboxyalkylaryloxy and lower alkoxy;

R$^{8A}$=hydrogen, hydroxy, O-alkyl;

R$^{9A}$=hydrogen, hydroxy, O-alkyl;

R$^{10A}$=hydrogen, lower alkyl, alkylaryl, aryl;

R$^{11A}$=hydrogen, lower alkyl, alkylaryl, aryl;

R$^{10A}$ and R$^{11A}$, taken together, may be alkylene, resulting in a N-containing heterocycle.

WO 95/11231 and WO 96/14844 also teaches that similar compounds serve as a nitrogen monoxide synthase inhibitor.

SUMMARY OF THE INVENTION

As a result of extensive studies, the inventors have found that compounds represented by formula (I) inhibit a nitrogen monoxide synthase, especially i-NOS. The present invention has been completed based on this finding.

The present invention relates to:

(1) a compound represented by formula (I):

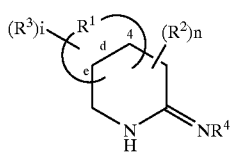

(I)

wherein

—R$^1$— represents a 3- or 4-membered carbocyclic ring together with the carbon atom or atoms to which it is bonded, said carbocyclic ring being condensed to side d or e of the piperidine ring or bonded to the 4-position of the piperidine ring through a spiro-union;

R$^2$ represents a C$_{1-6}$ alkyl group;

R$^3$ represents a C$_{1-6}$ alkyl group, a C$_{2-6}$ alkenyl group, a C$_{2-6}$ alkynyl group or a halogen atom;

R$^4$ represents a hydrogen atom, an amino-C$_{1-4}$ alkyl group or a carbocyclic ring-C$_{1-4}$ alkyl group which may be substituted with an amino-C$_{1-4}$ alkyl group;

i represents an integer of 0 to 3;

n represents an integer of 0 to 3; and the plural R$^2$'s or R$^3$'s are the same or different, or an acid addition salt thereof or a hydrate thereof;

(2) a process for preparing the same; and (3) a nitrogen monoxide synthase inhibitory composition comprising the same as an active ingredient with a carrier or diluent.

DETAILED DESCRIPTION OF THE INVENTION

In formula (I), the 3- or 4-membered carbocyclic ring formed by —R$^1$— and the carbon atom or atoms to which it is bonded is a cyclopropane ring or a cyclobutane ring.

The compounds represented by formula (I) are divided into those represented by formulae (IA) and (IB) in which a condensed ring is on side e of the piperidine ring; those represented by formula (IC) and (ID) in which a condensed ring is on side d of the piperidine ring; and those represented by formulae (IE) and (IF) in which a spiro ring is at the 4-position of the piperidine ring.

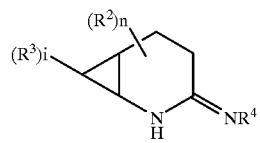

(IA)

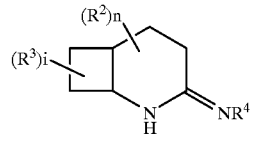

(IB)

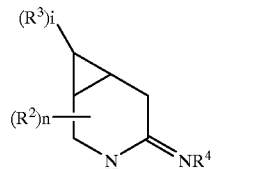

(IC)

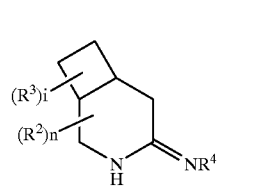

(ID)

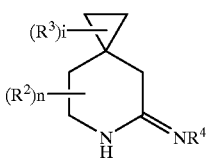

(IE)

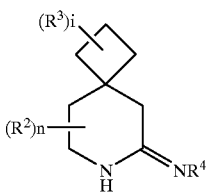

(IF)

The $C_{1-6}$ alkyl group represented by $R^2$ or $R^3$ includes methyl, ethyl, propyl, butyl, pentyl, hexyl, and isomers thereof.

The $C_{1-4}$ alkyl moiety in $R^4$ includes methyl, ethyl, propyl, butyl, and isomers thereof.

The $C_{2-6}$ alkenyl group represented by $R^3$ includes vinyl, propenyl, butenyl, pentenyl, hexenyl, and isomers thereof.

The $C_{2-6}$ alkynyl group represented by $R^3$ includes ethynyl, propynyl, butynyl, pentynyl, hexynyl, and isomers thereof.

The halogen atom represented by $R^3$ includes fluorine, chloride, bromine and iodine.

The carbocyclic ring in $R^4$ includes a $C_{4-7}$ cycloalkyl group (e.g., cyclobutyl, cyclopentyl, cyclohexyl, cycloheptyl), a $C_{4-7}$ cycloalkenyl group (e.g., cyclobutenyl, cyclopentenyl, cyclohexenyl, cycloheptenyl) and a benzene ring (e.g., phenyl group).

The compounds represented by formula (I) and compounds represented by formula (I') are equivalent to each other as illustrated below.

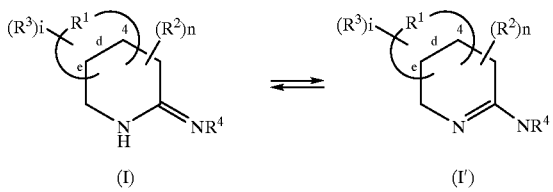

wherein all the symbols are as defined above.

Unless otherwise noted, all the possible isomers of the compounds are included under the scope of the present invention. For example, the alkyl group includes a straight-chain one and a branched one. All the isomers ascribed to an asymmetric carbon atom of, e.g., a branched alkyl group, are also included.

The compound represented by formula (I) can be converted to its acid addition salt in a conventional manner. It is desirable for the acid addition salt be non-toxic and water-soluble. Suitable acid addition salts include inorganic acid salts (e.g., hydrochloride, hydrobromide, hydroiodide, sulfate, phosphate, nitrate); and organic acid salts (e.g., acetate, lactate, tartrate, oxalate, fumarate, maleate, citrate, benzoate, methanesulfonate, ethanesulfonate, benzenesulfonate, toluenesulfonate, isethionate, glucuronate, gluconate).

The compound of formula (I) or a salt thereof can be converted to its hydrate in a known manner.

Process for Preparing the Compound of the Invention

The compound of formula (I) according to the present invention can be prepared by subjecting a compound represented by formula (II):

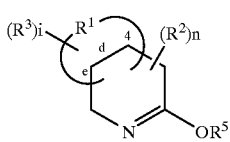

(II)

wherein $R^5$ represents a $C_{1-6}$ alkyl group; and other symbols are as defined above, to amidination reaction.

Amidination reaction is known. It is carried out by, for example, reacting the compound of formula (II) with ammonia and ammonium chloride or a compound represented by formula (III):

$$H_2N-R^{41} \qquad (III)$$

wherein $R^{41}$ represents an amino-$C_{1-4}$ alkyl group or a carbocyclic ring-$C_{1-4}$ alkyl group which may be substituted with an amino-$C_{1-4}$ alkyl group, in an alcohol solvent (e.g., methanol, ethanol, isopropanol) at 0 to 150° C.

The compound represented by formula (II) is prepared through Reaction Schemes A to F shown below according to the kinds of $R^1$ and $R^3$. The symbols used in the reaction schemes are as defined above or have the following meanings:

$R^{21}$: hydrogen or $C_{1-6}$ alkyl group;

$R^{22}$: hydrogen or $C_{1-6}$ alkyl group;

$R^{23}$: hydrogen or $C_{1-6}$ alkyl group;

$R^{31}$: $C_{1-6}$ alkyl group;

$R^{32}$: $C_{1-6}$ alkyl group;

$X^1$: halogen;

$X^2$: halogen;

$X^{10}$: halogen;

$Bu_3SnH$: tributyltin hydride;

$Ph_3SnH$: triphenyltin hydride;

AIBN: 2,2'-azobisisobutyronitrile;

$BF_3.OEt_2$: boron trifluoride diethyl ether complex;

PhSMe: thioanisole;

TFA: trifluoroacetic acid;

$Bu_2CuLi$: dibutylcopper lithium;

HMPA: hexamethylphosphoramide;

mCPBA: m-chloroperbenzoic acid;

aliquat-336: tricaprylylmethylammonium chloride;

PMB: p-methoxybenzyl.

Reaction Scheme A
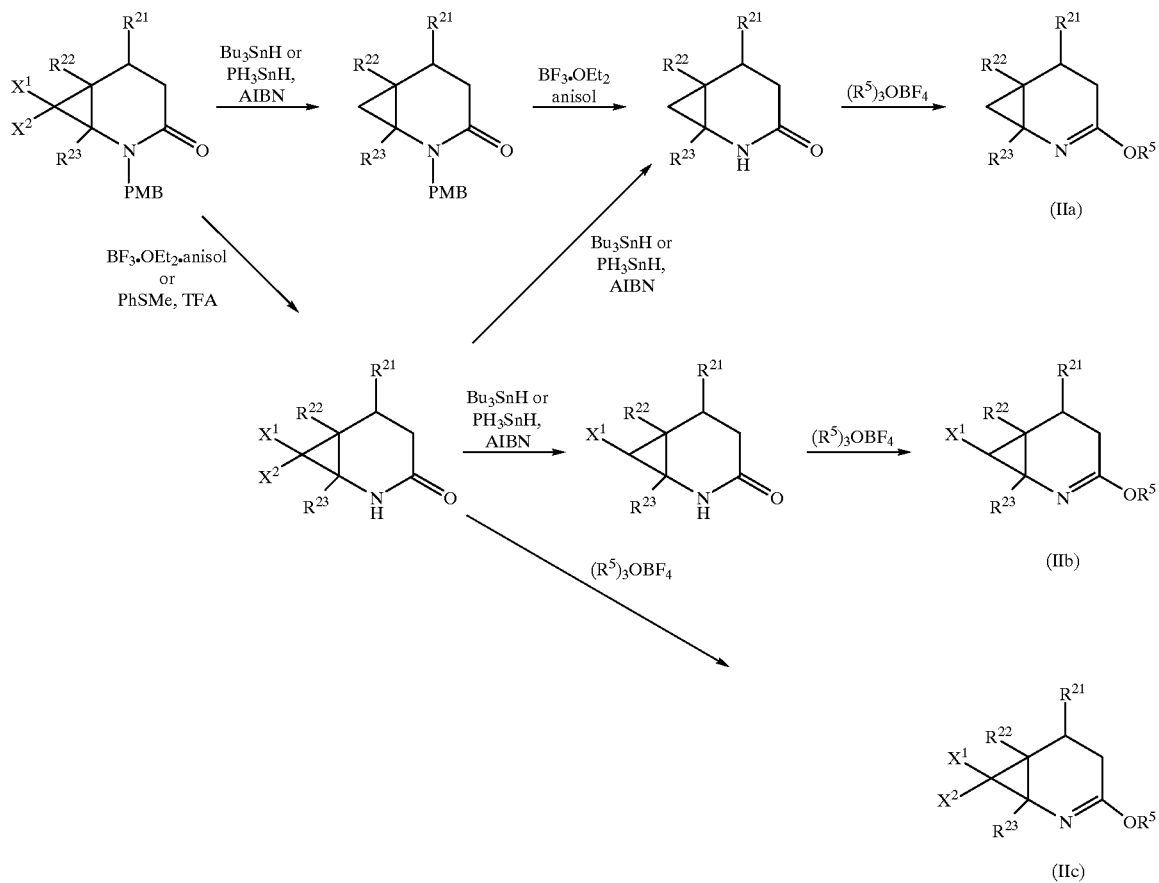
Reaction Scheme B
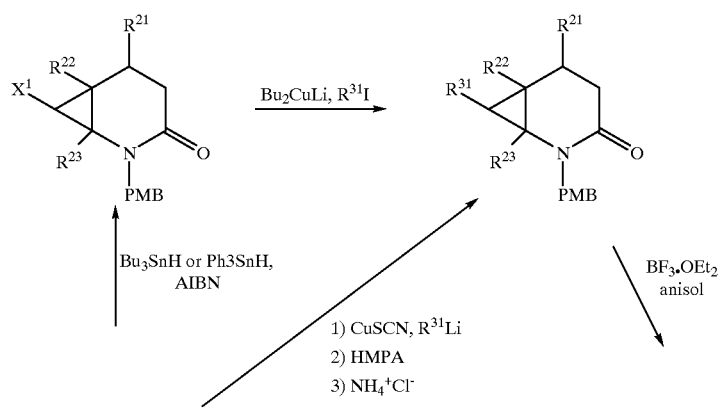

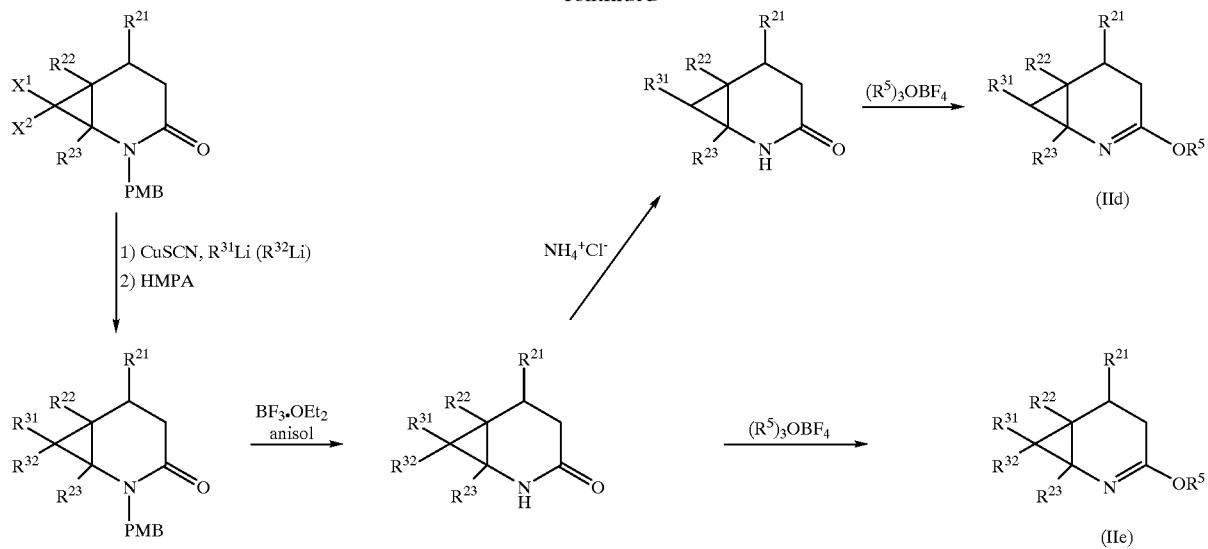
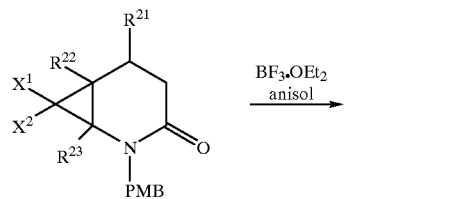
Reaction Scheme C
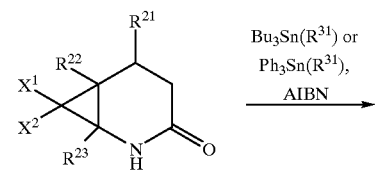
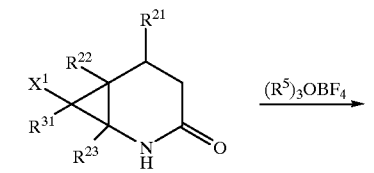
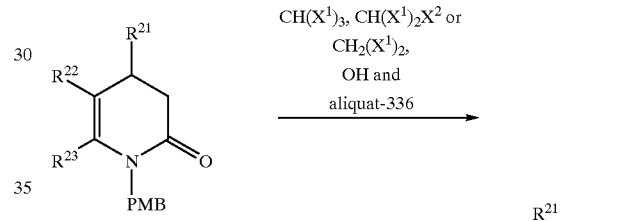
Reaction Scheme D
Reaction Scheme E
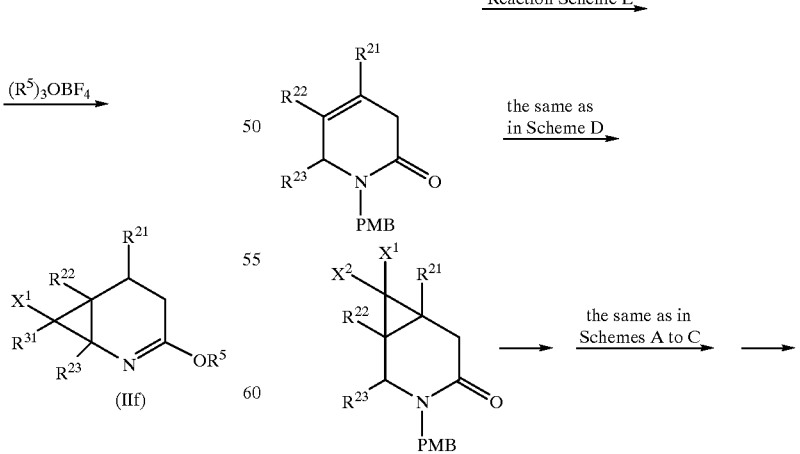

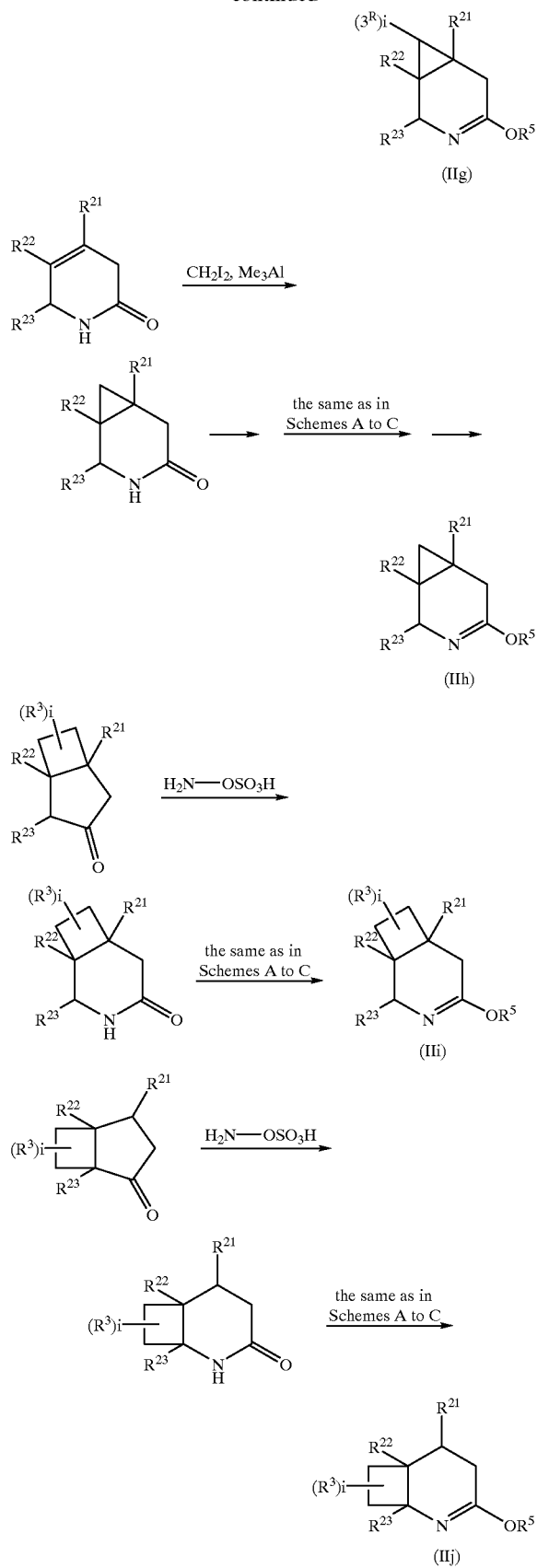

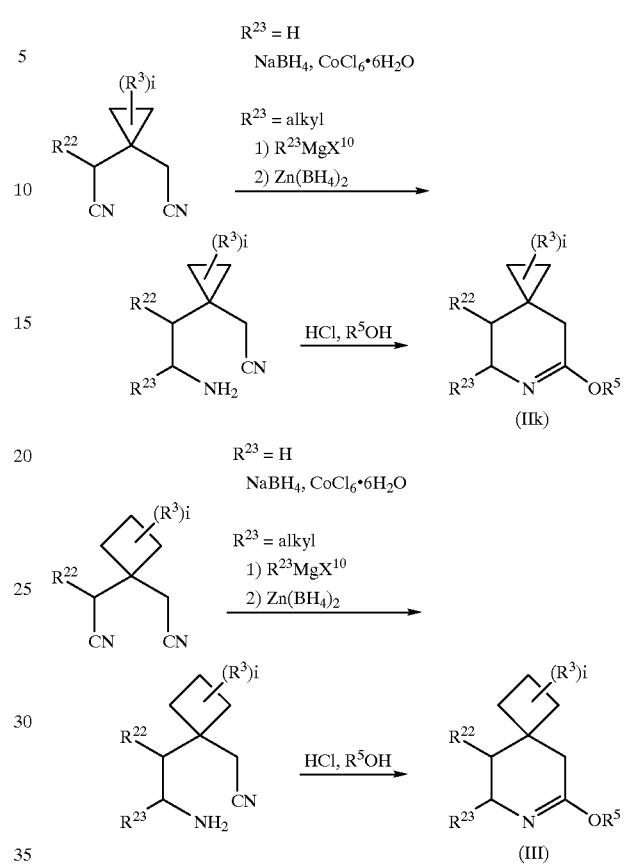

The starting compounds used in Reaction Schemes A to F are known or can be easily prepared from known compounds by known processes. Other starting materials or reagents used in the present invention are also known or can easily be prepared by known processes.

The reaction product obtained in each reaction described in the present invention can be purified by customary purification means, such as distillation under atmospheric pressure or reduced pressure, high performance liquid chromatography on silica gel or magnesium silicate, thin layer chromatography, column chromatography, washing, recrystallization and so on. The purification may be carried out for every reaction or after a series of a few reactions.

Application to Pharmaceutical Compositions

The compounds of formula (I) and their acid addition salts and hydrates thereof have an inhibitory action on nitrogen monoxide synthase. Therefore, they are expected to be useful in the treatment and/or prevention of diseases induced by a nitrogen monoxide synthase, for example, septicemia, endotoxin shocks, myocarditis, heart failure, multiple organ failure, systemic inflammatory response syndrome, shocks, tuberculosis, hypotension, rheumatic inflammation, chronic articular rheumatism, arthritis deformans, ulcerative colitis, stress-induced peptic ulcer, Crohn disease, autoimmune diseases, post-transplantation tissue disturbances and graft rejection, disturbances in re-perfusion after ischemia, acute obstruction of coronary micro blood vessels, shock-induced obstruction of blood vessels (disseminated intravascular coagulation syndrome (DIC), etc.), cerebral ischemic disturbances, arteriosclerosis, pernicious anemia, Fanconi's anemia, sickle-cell anemia, pancreatitis, nephrotic syndrome, Leishmania, glomerulonephritis, insulin dependent diabetes mellitus, hepatic porphyria, alcoholism, Parkinson's disease, chronic leukemia, acute leukemia, tumor, side effects of anticancer agents, infantile or adult dyspnea syndrome, pulmonary emphysema, Alzheimer's disease, disseminated sclerosis, vitamin E deficiency, aging, sunburn, muscular dystrophy, cataract, influenza infection, malaria, AIDS, radiation injury, and burn, and for improvement of efficiency of in vitro fertilization.

That is, the present invention relates to a pharmaceutical composition comprising a compound represented by formula (I), a non-toxic salt thereof or a hydrate thereof with a pharmaceutically acceptable carrier or diluent.

When an effective amount of the compounds of the present invention, non-toxic salts thereof, and hydrates thereof is used for the above-described purposes, they are usually administered to human or animals orally or non-orally and systemically or topically. The dosage varies depending on the age and body weight of a patient, the symptoms, the effect of treatment, the administration route, the period of treatment, and the like. The compound is usually administered orally at a dose level of 1 mg to 1000 mg/dose once or a few times per day for an adult or non-orally (preferably intravenously or intracerebralventricularly) at a dose level of 100 μg to 100 mg/dose once or a few times per day for an adult. Since the dosage depends on various factors as stated above, lower doses may be sufficient, or higher doses may be required.

In administering the compound of the present invention, it is formulated into solid compositions, liquid compositions or other compositions for oral administration or injectable preparations, external preparations, suppositories, etc. for non-oral administration.

The solid compositions for oral administration include tablets, pills, capsules, powders, and granules. The solid compositions are prepared by mixing at least one active ingredient with at least one inert diluent, such as lactose, mannitol, glucose, hydroxypropyl cellulose, microcrystalline cellulose, starch, polyvinylpyrrolidone, magnesium metasilicate aluminate, etc.

The solid compositions can contain customarily employed additives other than the inert diluent, such as lubricants (e.g., magnesium stearate), disintegrants (e.g., cellulose calcium glycolate), dissolution aids (e.g., arginine, glutamic acid, aspartic acid), and stabilizers (e.g., human serum albumin, lactose).

The tablets or pills, if desired, can be coated with a film of a gastric or enteric substance (e.g., sucrose, gelatin, hydroxypropyl cellulose, hydroxypropylmethyl cellulose phthalate).

The capsules include hard capsules and soft capsules.

The liquid compositions for oral administration include solutions, emulsions, suspensions, syrups, and elixirs. The liquid compositions for oral administration can contain generally used inert diluents (e.g., purified water, ethanol). If desired, the liquid compositions can contain adjuvants, such as wetting agents and suspending agents, sweeteners, flavors, aromatics, and antiseptics in addition to the inert diluents.

Other compositions for oral administration include sprays containing one or more active ingredients, which are prepared in a conventional manner. Sprays can contain stabilizers (e.g., sodium sulfite) and buffers for making the composition isotonic (e.g., sodium chloride, sodium citrate, citric acid) as well as inert diluents. The sprays can be prepared by the methods described in U.S. Pat. Nos. 2,868,691 and 3,095,355.

The injectable preparations for non-oral administration include sterile aqueous or nonaqueous solutions, suspension or emulsions.

The injectable preparations are prepared by mixing at least one active ingredient with at least one inert aqueous diluent (e.g., distilled water for injections, physiological saline) or inert nonaqueous diluent (e.g., propylene glycol, polyethylene glycol, olive oil, ethanol, Polysorbate 80 (registered trade name)). They can further contain antiseptics and adjuvants, such as wetting agents, emulsifiers, dispersants, stabilizers (e.g., human serum albumin, lactose), dissolution aids (e.g., arginine, glutamic acid, aspartic acid, polyvinylpyrrolidone), and the like.

The resulting liquid compositions are usually sterilized by filtration through a bacteria-trapping filter, etc., incorporation of bactericides or irradiation. The sterilized composition may be solidified by, for example, freeze-drying, to obtain a solid composition, which is dissolved in aseptic water or aseptic diluent on use.

The present invention will now be illustrated in greater detail with reference to Reference Examples, Preparation Examples, Formulation Example, and Test Examples, but it should be understood that the present invention is not construed as being limited thereto. The eluting solvents or developing solvents used in chromatographic separation are shown in parentheses, with the ratios given by volume.

REFERENCE EXAMPLE 1 dl-Trans-3-oxo-5-methyl-7,7-dibromo-2-(p-methoxybenzyl)-2-azabicyclo[4.1.0]heptane

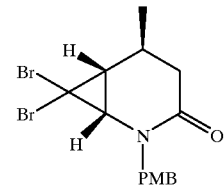

To a mixed solution of 1.6 g of 4-methyl-1-(4-methoxyphenylmethyl)-1,2,3,4-tetrahydropyridin-2-one, 20 ml of bromoform, and 0.05 g of aliquat-336 was added 6.4 g of a 50% sodium hydroxide aqueous solution in an argon atmosphere. The reaction mixture was stirred at room temperature for 24 hours. After completion of the reaction, 20 ml of a saturated ammonium chloride aqueous solution was added to the reaction mixture, and the mixture was extracted with ethyl acetate. The organic layer was washed, dried, and concentrated under reduced pressure. The residue was purified by silica gel column chromatography to give 1.68 g of the title compound, which had the following physical properties.

TLC: Rf 0.38 (hexan:ethyl acetate=2:1);

NMR (CDCl$_3$): δ7.29 (2H, d, J=8.4 Hz), 6.89 (2H, d, J=8.4 Hz), 5.46 (1H, d, J=14.8 Hz), 3.81 (1H, d, J=14.8 Hz), 3.81 (3H, s), 2.98 (1H, d, J=9.8 Hz), 2.40–2.00 (3H, m), 1.77 (1H, dd, J=9.8, 5.4 Hz), 1.26 (3H, s)

REFERENCE EXAMPLE 2 dl-Trans-3-oxo-5,7,7-trimethyl-2-(p-methoxybenzyl)-2-azabicyclo[4.1.0]heptane

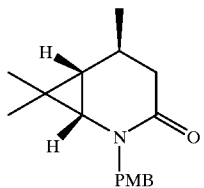

To a suspension of 4.82 g of copper thiocyanate in 30 ml of anhydrous diethyl ether was added dropwise 77 ml of a 1.03M solution of methyllithium in diethyl ether at −78° C. in an argon atmosphere. The temperature of the reaction mixture was elevated up to −10° C. over a period of 1.5 hours while stirring the mixture and then dropped to −20° C. A solution of 2.0 g of the compound prepared in Reference Example 1 in 40 ml of diethyl ether was added thereto dropwise. To the reaction mixture was further added 1.4 ml of hexamethylphosphoramide, followed by stirring at −20° C. for 1.5 hours. The reaction mixture was cooled to −50° C., and 10 ml of methyl iodide was added thereto, followed by stirring for an additional 30 minute period. A saturated ammonium chloride aqueous solution was added thereto, and the reaction mixture was filtered using Celite. The filtrate was washed, dried, and concentrated under reduced pressure. The residue was purified by silica gel column chromatography to give 1.0 g of the title compound, which had the following physical properties.

TLC: Rf 0.55 (hexane:ethyl acetate=1:1)

NMR (CDCl$_3$): δ7.22 (2H, d, J=8.8 Hz), 6.85 (2H, d, J=8.8 Hz), 5.14 (1H, d, J=14 Hz), 3.79 (1H, d, J=14 Hz), 3.79 (3H, s), 2.29–2.01 (3H, m), 1.78 (1H, m), 1.10 (3H, d, J=6.6 Hz), 1.00 (3H, s), 0.86 (3H, s), 0.69 (1H, dd, J=8.6 Hz, 6.2 Hz)

REFERENCE EXAMPLE 3 dl-Trans-3-oxo-5,7,7-trimethyl-2-azabicyclo[4.1.0]heptane

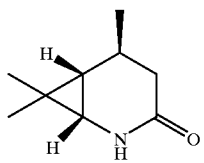

To a solution of 1.44 g of the compound prepared in Reference Example 2 in 2.3 ml of anisole was added 5.3 ml of a boron trifluoride diethyl ether complex in an argon atmosphere, and the mixture was stirred at 100° C. for 37 hours. After allowing to cool, the reaction mixture was poured into ice-water and extracted with chloroform. The organic layer was washed with a saturated sodium hydrogencarbonate aqueous solution, dried, and concentrated under reduced pressure. The residue was purified by silica gel column chromatography to give 410 mg of the title compound, which had the following physical properties.

TLC: Rf 0.15 (hexane:ethyl acetate=1:2);

NMR (CDCl$_3$): δ5.80 (1H, br), 2.36 (1H, d, J=8.4 Hz), 2.14 (1H, dd, J=14 Hz, 4 Hz), 1.98 (1H, dd, J=14 Hz, 12 Hz), 1.73 (1H, m), 1.15 (3H, d, J=6.6 Hz), 1.04 (3H, s), 0.99 (3H, s), 0.71 (1H, dd, J=8.4 Hz, 6 Hz)

REFERENCE EXAMPLE 4 dl-Trans-3-ethoxy-5,7,7-trimethyl-2-azabicyclo[4.1.0]hept-2-ene

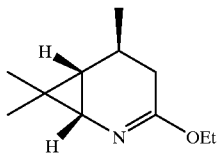

To a solution of 400 mg of the compound prepared in Reference Example 3 in 0.5 ml of anhydrous methylene chloride was added 1.5 ml of a 2.0M methylene chloride solution of a Meerwein's reagent in an argon atmosphere, and the mixture was stirred at room temperature for 15 hours. Concentration of the reaction mixture under reduced pressure gave the title compound, which was used for the subsequent reaction without purification.

Preparation Example 1 dl-Trans-3-imino-5,5,7-trimethyl-2-azabicyclo[4.1.0]heptane Monohydrochloride

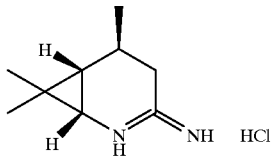

To the compound obtained in Reference Example 4 was added 0.5 ml of absolute ethanol in an argon atmosphere. After stirring for 10 minutes, 3 ml of a saturated ethanolic solution of ammonia was added thereto, followed by stirring for 8 hours. The reaction mixture was concentrated under reduced pressure, and chloroform was added to the concentrate. The solution was filtered, and the filtrate was concentrated under reduced pressure. The residue was purified by silica gel column chromatography. The resulting oily substance was dissolved in chloroform, and the solution was washed successively with a diluted sodium hydroxide aqueous solution and a saturated sodium chloride aqueous solution, and dried. To the solution was added 1 ml of 4N hydrochloric acid, and the solution was stirred for 30 minutes, followed by concentration under reduced pressure. The residue was purified by silica gel column chromatography to give 125 mg of the title compound, which had the following physical properties.

TLC: Rf 0.46 (chloroform:methanol:acetic acid=15:2:1);

NMR (DMSO-d$_6$): δ9.40 (1H, br), 8.99 (1H, br), 8.71 (1H, br), 2.74 (1H, dd, J=15 Hz, 3 Hz), 2.45 (1H, d, J=8 Hz), 2.10 (1H, m), 1.74 (1H, m), 1.22 (3H, d, J=6.6 Hz), 1.07 (3H, s), 0.99 (3H, s), 0.83 (1H, dd, J=8 Hz, 6 Hz)

Preparation Example 1(a)

dl-Trans-3-imino-1,5,7,7-tetramethyl-2-azabicyclo[4.1.0]heptane Monohydrochloride

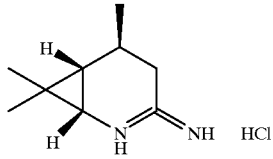

The title compound having the following physical properties was obtained in the same manner as in Reference Examples 1 to 4 and Preparation Example 1.

TLC: Rf 0.49 (chloroform methanol:acetic acid=20:4:1);

NMR (DMSO-$d_6$): δ9.80 (1H, br), 9.06 (1H, br), 8.57 (1H, br), 2.42–2.17 (2H, m), 1.67 (1H, m), 1.36 (3H, s), 1.13 (3H, d, J=5.8 Hz), 1.12 (3H, s), 0.90 (3H, s), 0.59 (1H, d, J=5.6 Hz)

REFERENCE EXAMPLE 5 dl-Trans-3-oxo-5,7-dimethyl-2-(p-methoxybenzyl)-2-azabicyclo[4.1.0]heptane

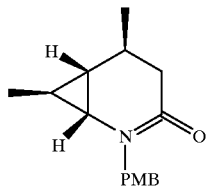

To a suspension of 6.03 g of copper thiocyanate in 35 ml of anhydrous diethyl ether was added dropwise 96 ml of a 1.03M solution of methyllithium in diethyl ether at −78° C. in an argon atmosphere. The temperature of the reaction mixture was elevated up to −10° C. over a period of 1.5 hours while stirring the mixture and then dropped to −20° C. A solution of 2.5 g of the compound prepared in Reference Example 1 in 45 ml of anhydrous diethyl ether was added thereto dropwise, and the mixture was stirred at −20° C. for 1.5 hours. The reaction mixture was cooled to −50° C., and a saturated ammonium chloride aqueous solution was added thereto, followed by filtration using Celite. The filtrate was washed successively with diluted aqueous ammonia and a saturated sodium chloride aqueous solution, dried, and concentrated under reduced pressure. The residue was purified by silica gel column chromatography to give 636 mg of the title compound, which had the following physical properties.

TLC: Rf 0.38 (hexane:ethyl acetate=1:1);

NMR (CDCl$_3$): δ7.23 (2H, d, J=8.8 Hz), 6.85 (2H, d, J=8.8 Hz), 4.76 (1H, d, J=14.2 Hz), 4.36 (1H, d, J=14.2 Hz), 3.80 (3H, s), 2.28–2.04 (3H, m), 1.73 (1H, m), 1.13 (3H, d, J=6.6 Hz), 0.71 (3H, d, J=6.2 Hz), 0.68 (1H, m), 0.57 (1H, m)

REFERENCE EXAMPLE 6 dl-Trans-3-oxo-5,7-dimethyl-2-azabicyclo[4.1.0]heptane

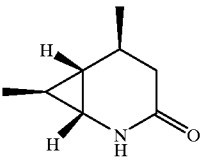

To a solution of 730 mg of the compound prepared in Reference Example 5 in 1.2 ml of anisole was added 2.8 ml of a boron trifluoride diethyl ether complex in an argon atmosphere, followed by stirring at 100° C. for 37 hours. After being allowed to cool, the reaction mixture was poured into ice-water and extracted with chloroform. The organic layer was washed with a saturated sodium hydrogencarbonate aqueous solution, dried, and concentrated under reduced pressure. The residue was purified by silica gel column chromatography to give 307 mg of the title compound, which had the following physical properties.

NMR (CDCl$_3$): δ6.12 (1H, br), 2.32 (1H, ddd, J=8.4 Hz, 3.0 Hz, 1.8 Hz), 2.14 (1H, dd, J=15 Hz, 5.8 Hz), 2.01 (1H, d, J=15 Hz), 1.86 (1H, m), 1.18 (3H, d, J=6.6 Hz), 1.02 (3H, d, J=5.8 Hz), 0.81 (1H, m), 0.71 (1H, m)

Preparation Example 2 dl-Trans-3-imino-5,7-dimethyl-2-azabicyclo[4.1.0]heptane Monohydrochloride

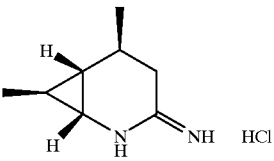

The title compound having the following physical properties was prepared from the compound obtained in Reference Example 6 in the same manner as in Reference Example 4 and Preparation Example 1.

TLC: Rf 0.40 (chloroform:methanol:acetic acid=15:2:1);

NMR (CDCl$_3$): δ9.80 (1H, br), 9.22 (1H, br), 8.72 (1H, br), 2.66 (1H, dd, J=16 Hz, 4 Hz), 2.43 (1H, dd, J=8 Hz, 3 Hz), 2.29 (1H, dd, J=16 Hz, 9 Hz), 1.91 (1H, m), 1.21 (3H, d, J=6.8 Hz), 1.05 (3H, d, J=5.2 Hz), 0.96 (1H, m), 0.85 (1H, m)

Preparation Examples 2(a) to 2(i)

The following compounds having the following physical properties were obtained in the same manner as in Reference Example 4 and Preparation Example 1.

Preparation Example 2(a)

dl-Trans-3-imino-5-methyl-7-butyl-2-azabicyclo
[4.1.0]heptane Monohydrochloride

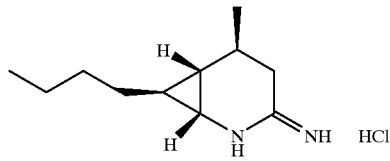

TLC: Rf 0.55 (chloroform:methanol:acetic acid=15:2:1);

NMR (CDCl$_3$): δ9.83 (1H, br), 8.99 (1H, br), 8.88 (1H, br), 2.64 (1H, dd, J=16 Hz, 4 Hz), 2.47 (1H, dd, J=8 Hz, 3 Hz), 2.29 (1H, dd, J=16 Hz, 9 Hz), 1.88 (1H, m), 1.40–1.25 (5H, m), 1.21 (3H, d, J=6.8 Hz), 1.10 (1H,m), 1.0–0.8 (5H, m)

Preparation Example 2(b)

dl-Trans-3-imino-5-methyl-7-ethyl-2-azabicyclo
[4.1.0]heptane Monohydrochloride

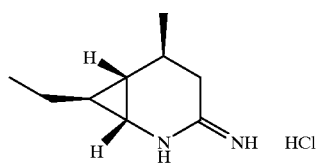

TLC: Rf 0.45 (chloroform:methanol:acetic acid=10:1:1);

NMR (DMSO-d$_6$): δ9.89 (1H, br s), 8.84 (1H, br s), 8.44 (1H, br s), 2.58–2.46 (1H, m), 2.46–2.38 (1H, m), 2.22 (1H, dd, J=7.2, 16 Hz), 2.10–1.91 (1H, m), 1.27–1.17 (2H, m), 1.08 (3H, d, J=6.6 Hz), 1.03–0.85 (2H, m), 0.92 (3H, t, J=6.6 Hz)

Preparation Example 2(c)

dl-Trans-3-imino-1,5,7-trimethyl-2-azabicyclo[4.1.0]
heptane Monohydrochloride

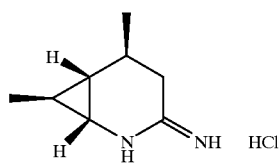

TLC: Rf 0.35 (chloroform:methanol:acetic acid=20:1:1);

NMR (DMSO-d$_6$): δ10.17 (1H, br), 8.89 (1H, br), 8.46 (1H,br), 2.42 (1H, dd, J=16.4, 5.4 Hz), 2.24 (1H, dd, J=16.4, 7.4 Hz), 1.98 (1H, m), 1.31 (3H, s), 1.20–0.90 (1H, m), 1.02 (6H, m), 0.62 (1H, m)

Preparation Example 2(d)

dl-Trans-3-imino-5-methyl-7-butyl-2-azabicyclo
[4.1.0]heptane Monohydrochloride

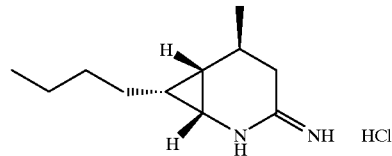

TLC: Rf 0.53 (chloroform methanol:acetic acid=15:2:1);

NMR (CDCl$_3$): δ9.62 (1H, br), 9.15 (1H, br), 9.01 (1H, br), 2.81–2.71 (2H, m), 2.17 (1H, dd, J=16 Hz, 12 Hz), 1.73 (1H, m), 1.42–1.25 (6H, m), 1.23 (3H, d, J=6.6 Hz), 1.12–1.00 (2H, m), 0.91 (3H, t, J=6.2 Hz)

Preparation Example 2(e)

dl-Trans-3-imino-5-methyl-7-propyl-2-azabicyclo
[4.1.0]heptane Monohydrochloride

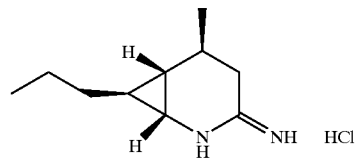

TLC: Rf 0.47 (chloroform:methanol:acetic acid=20:2:1);

NMR (CDCl$_3$): δ9.90–9.80 (1H, br), 9.00–8.85 (1H, br), 8.85–8.70 (1H, br), 2.62 (1H, dd, J=4.4, 16.4 Hz), 2.53–2.41 (1H, m), 2.28 (1H, dd, J=9.4, 16.4 Hz), 2.00–1.80 (1H, br), 1.50–1.28 (3H, m), 1.21 (3H, d, J=7.0 Hz), 1.16–1.00 (1H, m), 1.00–0.80 (5H, m)

Preparation Example 2(f)

dl-Trans-3-imino-5-methyl-7-vinyl-2-azabicyclo
[4.1.0]heptane Monohydrochloride

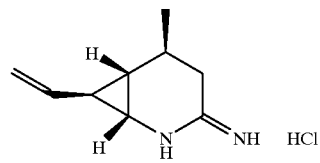

TLC: Rf 0.35 (chloroform:methanol:acetic acid=20:4:1);

NMR (DMSO-d$_6$): δ10.07 (1H, br), 9.01 (1H, br), 8.61 (1H, br), 5.49 (1H, ddd, J=8.4, 10.2, 17.2 Hz), 5.08 (1H, dd, J=1.8, 17.2 Hz), 4.95 (1H, dd, J=1.8, 10.2 Hz), 2.88 (1H, dt, J=3.0, 8.4 Hz), 2.54 (1H, m), 2.28 (1H, dd, J=7.0, 16.0 Hz), 2.11 (1H, m), 1.82 (1H,m), 1.29 (1H, m), 1.09 (3H, d, J=6.6 Hz)

Preparation Example 2(g)

dl-Trans-3-imino-5, 7-dimethyl-2-azabicyclo [4.1.] heptane Monohydrochloride

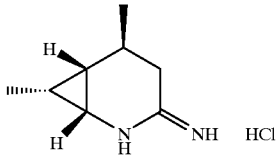

TLC: Rf 0.15 (chloroform:methanol:acetic acid=20:1:1);

NMR (DMSO-d$_6$): δ9.75 (1H, br), 8.97 (1H, br), 8.77 (1H, br), 2.66 (1H, dd, J=8.0, 6.0 Hz), 2.30 (1H, dd, J=15.5, 4.0 Hz), 2.19 (1H, dd, J=15.5, 11.5 Hz), 1.56 (1H, m), 1.08 (3H, d, J=6.5 Hz), 1.12–1.02 (1H, m), 1.00–0.88 (1H, m), 0.79 (3H, d, J=6.0 Hz)

Preparation Example 2(h)

dl-Trans-3-imino-5-methyl-7-ethyl-2-azabicyclo [4.1.0]heptane Monohydrochloride

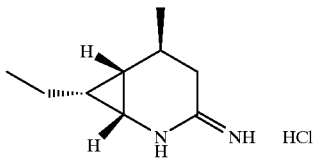

TLC: Rf 0.48 (chloroform:methanol:acetic acid=15:2:1);

NMR (CDCl$_3$): δ9.64 (1H, br), 9.35 (1H, br), 8.90 (1H, br), 2.90–2.70 (2H, m), 2.15 (1H, dd, J=16 Hz, 12 Hz), 1.77 (1H, m), 1.40–1.20 (2H, m), 1.24 (3H, d, J=6.6 Hz), 1.12–0.96 (2H, m), 1.01 (3H, t, J=6.8 Hz)

Preparation Example 2(i)

(+)-Trans-3-imino-5,7-dimethyl-2-azabicyclo [4.1.0] heptane Monohydrochloride

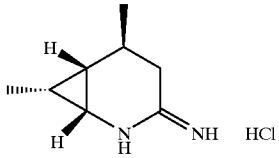

TLC: Rf 0.50 (chloroform:methanol:acetic acid=5:1:1);

NMR (DMSO-d$_6$): δ9.70–9.65 (1H, brs), 9.20–9.00 (1H, brs), 8.70–8.60 (1H, brs), 2.73 (1H, t, J=7.5 Hz), 2.45–2.15 (2H, m), 1.80–1.50 (1H, m), 1.15 (3H, d, J=7.0 Hz), 1.20–0.90 (2H, m), 0.85 (3H, d, J=6.4 Hz)

REFERENCE EXAMPLE 7 dl-Trans-3-oxo-5-methyl-7-chloro-2-azabicyclo [4.1.0]heptane

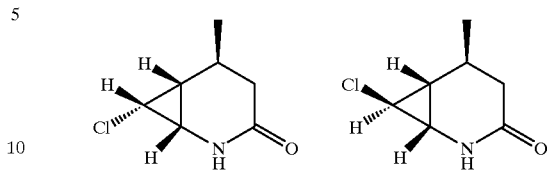

A mixture consisting of 818 mg of dl-trans-3-oxo-5-methyl-7,7-dichloro-2-azabicyclo[4.1.0]heptane (prepared in the same manner as described in Reference Examples 1 and 3), 5.4 ml of benzene, 1.64 g of triphenyltin hydride, and 34 mg of 2,2'-azobisisobutyronitrile was stirred at 80° C. for 4 hours in an argon atmosphere. After completion of the reaction, the reaction mixture was allowed to cooled to room temperature, and 10 ml of ethyl acetate and 10 ml of a 10% potassium fluoride aqueous solution were added thereto, followed by stirring for 10 minutes. The reaction mixture was filtered through Celite, and the filtrate was extracted with ethyl acetate. The extract was washed with a saturated sodium chloride aqueous solution, dried, and concentrated under reduced pressure. The residue was purified by silica gel column chromatography to furnish 484 mg of an α-chloro compound and 227 mg of a β-chloro compound, which had the following physical properties.

α-Chloro compound:
TLC: Rf 0.27 (hexane:ethyl acetate=1:5);
NMR (CDCl$_3$): δ6.10–5.80 (1H, br), 3.26 (1H, dd, J=7.8, 5.2 Hz), 2.86 (1H, dd, J=5.2, 1.2 Hz), 2.28–2.03 (3H, m), 1.36–1.25 (1H, m), 1.23 (3H, d, J=6.4 Hz)

β-Chloro compound:
TLC: Rf 0.41 (hexane:ethyl acetate=1:5);
NMR (CDCl$_3$): δ6.40–6.20 (1H, br), 2.94 (1H, dt, J=9.2, 2.0 Hz), 2.85 (1H, dd, J=3.6, 2.0 Hz), 2.25–1.90 (3H, m), 1.50–1.38 (1H, m), 1.26 (3H, d, J=6.6 Hz)

Preparation Example 3

(+)-Trans-3-imino-5-methyl-7-chloro-2-azabicyclo [4.1.0]heptane Monohydrochloride

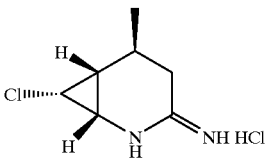

The title compound was obtained from the compound prepared in Reference Example 7 in the same manner as in Reference Example 4 and Preparation Example 1. The physical properties of the compound were as follows.

TLC: Rf 0.33 (chloroform:methanol:acetic acid=10:1:1);
NMR (DMSO-d$_6$): δ9.80–9.65 (1H, br), 9.30–9.10 (1H, br), 8.80–8.60 (1H, br), 3.64 (1H, dd, J=7.7, 5.5 Hz), 3.04 (1H, dd, J=8.9, 5.5 Hz), 2.41 (2H, d, J=8.2 Hz), 1.90–1.70 (1H, m), 1.55–1.40 (1H, m), 1.21 (3H, d, J=6.8 Hz);
Specific rotation: $[\alpha]^D$+81.4° (c=0.160, methanol)

Preparation Examples 3(a) to 3(p)

The following compounds having the following physical properties were obtained in the same manner as in Reference Examples 7 and 4 and Preparation Example 1.

Preparation Example 3(a)

dl-Trans-3-imino-5-methyl-2-azabicyclo[4.1.0] heptane Monohydrochloride

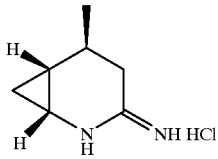

TLC: Rf 0.18 (chloroform:methanol:acetic acid=15:2:1);

NMR (DMSO-$d_6$): δ9.98 (1H, br), 8.95 (1H, br), 8.54 (1H, br), 2.82 (1H, m), 2.46 (1H, dd, J=16 Hz, 5 Hz), 2.27 (1H, dd, J=16 Hz, 7 Hz), 2.02 (1H, m), 1.2–1.0 (1H, m), 1.08 (3H, d, J=6.8 Hz), 0.88 (1H, m), 0.73 (1H, m)

Preparation Example 3(b)

(−)-Trans-3-imino-5-methyl-7-chloro-2-azabicyclo[4.1.0]heptane Monohydrochloride

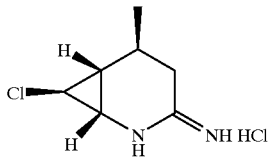

TLC: Rf 0.33 (chloroform:methanol:acetic acid=10:1:1);

NMR (DMSO-$d_6$): δ10.10–9.85 (1H, br), 9.20–9.00 (1H, br), 8.80–8.60 (1H, br), 3.58 (1H, dd, J=3.9, 2.0 Hz), 3.19 (1H, dd, J=9.4, 2.0 Hz), 2.45–2.38 (1H, m), 2.36–2.05 (2H, m), 1.75–1.56 (1H, m), 1.10 (3H, d, J=6.4 Hz);

Specific rotation: $[\alpha]^D$ −5.92 (C=0.385, methanol)

Preparation Example 3(c)

dl-Trans-3-imino-5-methyl-7α-chloro-2-azabicyclo[4.1.0]heptane Monohydrochloride

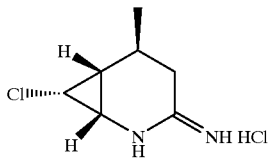

TLC: Rf 0.33 (chloroform:methanol:acetic acid=10:1:1);

NMR (DMSO-$d_6$): δ9.90 (1H, br), 9.33 (1H, br), 8.87 (1H, br), 3.64 (1H, dd, J=5.6, 7.8 Hz), 3.06 (1H, ddd, J=1.6, 5.6, 9.2 Hz), 2.54–2.39 (2H, m), 1.97–1.74 (1H, m), 1.55–1.41 (1H, m), 1.22 (1H, d, J=6.6 Hz)

Preparation Example 3(d)

dl-Trans-3-imino-5-methyl-7β-chloro-2-azabicyclo[4.1.0]heptane Monohydrochloride

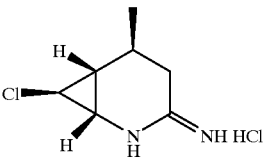

TLC: Rf 0.33 (chloroform:methanol:acetic acid=10:1:1);

NMR (DMSO-$d_6$): δ10.27 (1H, br), 9.26 (1H, br), 8.85 (1H, br), 3.59 (1H, dd, J=2.0, 3.8 Hz), 3.19 (1H, ddd, J=2.0, 2.4, 9.4 Hz), 2.58–2.45 (1H, m), 2.34–2.10 (2H, m), 1.68–1.57 (1H, m), 1.10 (1H, d, J=6.6 Hz)

Preparation Example 3(e)

(−)-Trans-3-imino-5-methyl-2-azabicyclo[4.1.0] heptane Monohydrochloride

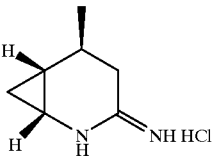

TLC: Rf 0.30 (chloroform:methanol:acetic acid=10:1:1);

NMR (DMSO-$d_6$): δ10.09 (1H, br), 9.02 (1H, br), 8.61 (1H, br), 2.88–2.76 (1H, m), 2.48 (1H, dd, J=5.0, 16.2 Hz), 2.27 (1H, dd, J=6.8, 16.2 Hz), 2.12–1.92 (1H, m), 1.20–1.04 (1H, m), 1.09 (3H, d, J=6.8 Hz), 0.88 (1H, ddd, J=5.6, 6.8, 8.8 Hz), 0.73 (1H, dt, J=3.4, 5.8 Hz);

Specific rotation: $[\alpha]^D$ −50.1 (c=0.265, methanol)

Preparation Example 3(f)

(+)-Trans-3-imino-5-methyl-2-azabicyclo[4.1.0] heptane Monohydrochloride

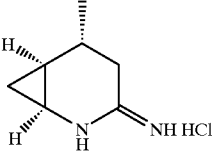

TLC: Rf 0.27 (chloroform:methanol:acetic acid=10:1:1);

NMR (DMSO-$d_6$): δ10.07 (1H, br s), 8.90 (1H, br s), 8.63 (1H, br s), 2.86–2.77 (1H, m), 2.53–2.42 (1H, m), 2.26 (1H, dd, J=7.0, 16 Hz), 2.07–1.96 (1H, m), 1.14–1.07 (1H, m), 1.09 (3H, d, J=7.0 Hz), 0.94–0.83 (1H, m), 0.76–0.69 (1H, m);

Specific rotation: $[\alpha]^D$ +53.2 (c=0.025, methanol)

Preparation Example 3(g)

dl-Cis-3-imino-5-methyl-2-azabicyclo[4.1.0]heptane Monohydrochloride

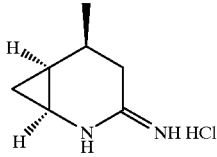

TLC: Rf 0.21 (chloroform:methanol:acetic acid=20:2:1);

NMR (DMSO-$d_6$): δ9.98 (1H, m), 8.72 (1H, m), 8.30 (1H, m), 2.90 (1H, m), 2.36 (1H, m), 2.20–1.98 (2H, m), 1.30 (1H, m), 1.02 (3H, d, J=6.2 Hz), 0.82 (1H, dt, J=6.4, 6.4, 3.4 Hz), 0.64 (1H, dt, J=9.2, 6.4, 6.4 Hz)

Preparation Example 3(h)

dl-Cis-3-imino-1,5-dimethyl-2-azabicyclo[4.1.0]heptane Monohydrochloride

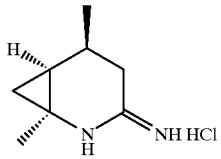

TLC: Rf 0.43 (chloroform:methanol:acetic acid=10:1:1);

NMR (DMSO-$d_6$): δ10.18 (1H, br), 8.75 (1H, br), 8.57 (1H, br), 2.80 (1H, m), 2.38–2.16 (1H, m), 2.00–1.78 (1H, m), 1.52 (3H, s), 1.32–1.18 (1H, m), 1.14 (3H, d, J=6.4 Hz), 0.82 (1H, m), 0.71 (1H, m)

Preparation Example 3(i)

dl-Trans-3-imino-1,5-dimethyl-2-azabicyclo[4.1.0]heptane Monohydrochloride

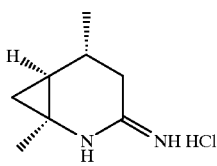

TLC: Rf 0.41 (chloroform:methanol:acetic acid=10:1:1);

NMR (DMSO-$d_6$): δ10.12 (1H, br), 8.92 (1H, br), 8.38 (1H, br), 2.44 (1H, dd, J=16.6, 5.4 Hz), 2.28 (1H, dd, J=16.6, 7.0 Hz), 1.98 (1H, m), 1.36 (3H, s), 1.06 (3H, d, J=7.0 Hz), 1.00–0.90 (1H, m), 0.85–0.81 (2H, m)

Preparation Example 3(j)

(+)-Trans-3-imino-5-methyl-7-fluoro-2-azabicyclo[4.1.0]heptane Monohydrochloride

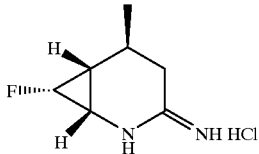

TLC: Rf 0.21 (chloroform:methanol:acetic acid=10:1:1);

NMR (DMSO-$d_6$): δ10.10–9.90 (1H, br), 9.50–9.20 (1H, br), 9.15–8.80 (1H, br), 4.78 (1H, ddd, J=65.6, 6.2, 4.4 Hz), 3.05–2.80 (1H, m), 2.60–2.28 (2H, m), 2.12–1.82 (1H, m), 1.45–1.15 (1H, m), 1.18 (3H, d, J=6.6 Hz);

Specific rotation: $[\alpha]^D$+57.5 (c=0.160, methanol)

Preparation Example 3(k)

(+)-Trans-3-benzylimino-5-methyl-7-chloro-2-azabicyclo[4.1.0]heptane Monohydrochloride

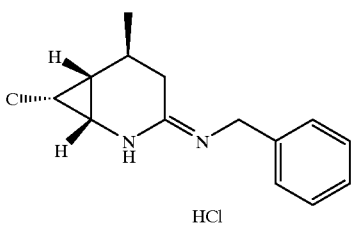

TLC: Rf 0.24 (chloroform:methanol=5:1);

NMR (DMSO-$d_6$): δ10.40–10.20 (1H, br), 10.05–9.90 (1H, br), 7.50–7.30 (5H, m), 4.53 (2H, br), 3.71 (1H, dd, J=7.7, 5.6 Hz), 3.12 (1H, dd, J=9.2, 5.6 Hz), 2.70–2.40 (2H, m), 2.00–1.80 (1H, m), 1.60–1.45 (1H, m), 1.23 (3H, d, J=7 Hz);

Specific rotation: $[\alpha]^D$+6.47 (c=0.4750, methanol)

Preparation Example 3(l)

(+)-Trans-3-(3-aminomethylbenzyl)imino-5-methyl-7-chloro-2-azabicyclo[4.1.0]heptane Dihydrochloride

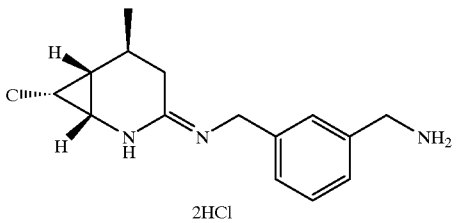

NMR (DMSO-$d_6$): δ10.40–10.30 (1H, br), 10.10–10.00 (1H, br), 8.60–8.30 (3H, br), 7.60–7.40 (3H, m), 7.40–7.30 (1H, m), 4.65–4.52 (2H, br), 4.08–3.94 (2H, br), 3.70 (1H, dd, J=7.6, 5.6 Hz), 3.12 (1H, dd, J=8.8, 5.6 Hz), 2.70–2.40 (2H, m), 2.00–1.80 (1H, m), 1.60–1.45 (1H, m), 1.23 (3H, d, J=6.8 Hz)

Preparation Example 3(m)

(−)-Cis-3-imino-5-methyl-7-fluoro-2-azabicyclo[4.1.0]heptane Monohydrochloride

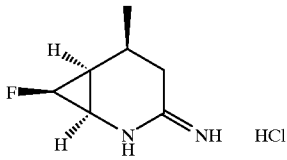

TLC: Rf 0.26 (chloroform:methanol:acetic acid=10:1:1);

NMR (DMSO-d$_6$): δ10.55–10.35 (1H, brs), 9.20–9.00 (1H, brs), 8.80–8.60 (1H, brs), 4.85 (1H, dt, J=64.6, 5.4 Hz), 3.25–3.00 (1H, m), 2.80–2.55 (1H, m), 2.45–2.20 (1H, m), 2.00–1.80 (1H, m), 1.60–1.35 (1H, m), 1.13 (3H, d, J=6.6 Hz)

Preparation Example 3(n)

(−)-Trans-3-imino-5-methyl-7-chloro-2-azabicyclo[4.1.0]heptane Monohydrochloride

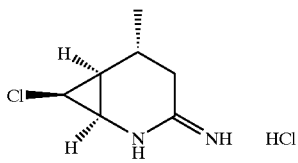

TLC: Rf 0.36 (chloroform:methanol:acetic acid=10:1:1);

NMR (DMSO-d$_6$): δ10.05–9.90 (1H, brs), 9.50–9.30 (1H, brs), 9.00–8.80 (1H, brs), 3.64 (1H, dd, J=7.8, 5.6 Hz), 3.05 (1H, dd, J=8.8, 5.6 Hz), 2.55–2.30 (2H, m), 1.96–1.72 (1H, m), 1.56–1.40 (1H, m), 1.20 (3H, d, J=6.6 Hz)

Preparation Example 3(o)

(+)-Cis-3-imino-5-methyl-7-chloro-2-azabicyclo[4.1.0]heptane Monohydrochloride

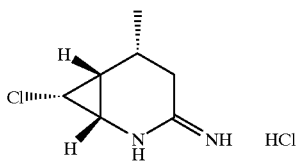

TLC: Rf 0.30 (chloroform:methanol:acetic acid=10:1:1);

NMR (DMSO-d$_6$): δ10.50–10.20 (1H, brs), 9.20–8.90 (1H, brs), 8.90–8.60 (1H, brs), 3.59 (1H, dd, J=8.0, 6.0 Hz), 3.40–3.10 (1H, m), 2.70 (1H, dd, J=16.7, 6.2 Hz), 2.50–2.30 (1H, m), 2.20 (1H, dd, J=16.7, 11.0 Hz), 1.80–1.60 (1H, m), 1.16 (3H, d, J=6.6 Hz)

Preparation Example 3(p)

(+)-Cis-3-imino-5-methyl-7-fluoro-2-azabicyclo[4.1.0]heptane Monohydrochloride

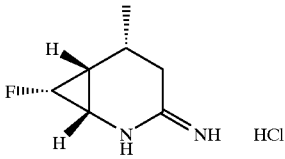

TLC: Rf 0.28 (chloroform:methanol:acetic acid=20:4:1);

NMR (CDCl$_3$): δ10.8–10.3 (1H, br), 8.81 (2H, brs), 4.67 (1H, m), 3.12–2.75 (2H, m), 2.45–2.10 (2H, m), 1.50–1.25 (1H, m), 1.26 (3H, d, J=6.0 Hz)

Preparation Example 4

(+)-Trans-3-imino-5-methyl-7,7-dichloro-2-azabicyclo[4.1.0]heptane Monohydrochloride

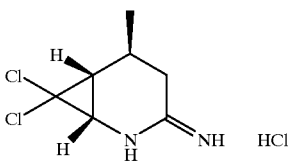

The title compound having the following physical properties was obtained from dl-trans-3-oxo-5-methyl-7,7-dichloro-2-azabicyclo[4.1.0]heptane in the same manner as in Reference Example 4 and Preparation Example 1.

TLC: Rf 0.35 (chloroform:methanol:acetic acid=10:1:1);

NMR (DMSO-d$_6$): δ10.41 (1H, br), 9.70 (1H, br), 7.25 (1H, br), 3.55 (1H, d, J=9.8 Hz), 2.53 (1H, dd, J=5.0, 15.6 Hz), 2.36 (1H, dd, J=11.8, 15.6 Hz), 2.12 (1H, dd, J=5.4, 9.8 Hz), 2.03–1.80 (1H, m), 1.27 (3H, d, J=6.6 Hz);

Specific rotation: $[\alpha]^D$+44.6 (c=0.435, methanol)

Preparation Examples 4(a) to 4(c)

The following compounds having the following physical properties were obtained in the same manner as in Reference Example 4 and Preparation Example 1.

Preparation Example 4(a)

dl-Trans-7,7-dichloro-3-imino-5-methyl-2-azabicyclo[4.1.0]heptane Monohydrochloride

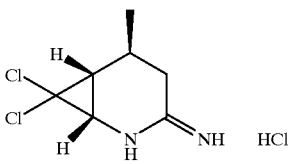

TLC: Rf 0.63 (chloroform:methanol:acetic acid=10 1:1);

NMR (CDCl$_3$+CD$_3$OD): δ3.40 (1H, d, J=9.6 Hz), 2.68 (1H, dd, J=15.6, 3.5 Hz), 2.29 (1H, dd, J=15.6, 12.5 Hz), 2.18–2.20 (1H, m), 1.94 (1H, dd, J=9.6, 5.1 Hz), 1.36 (3H, d, J=6.6 Hz)

Preparation Example 4(b)

(−)-Trans-3-imino-5-methyl-7,7-dichloro-2-azabicyclo[4.1.0]heptane Monohydrochloride

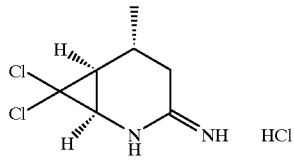

TLC: Rf 0.36 (chloroform:methanol:acetic acid=10:1:1);

NMR (DMSO-$d_6$): δ9.66 (3H, br s), 3.55 (1H, d, J=9.6 Hz), 2.57–2.28 (2H, m), 2.11 (1H, dd, J=5.6, 10 Hz), 2.01–1.84 (1H, m), 1.27 (3H, d, J=6.6 Hz);

Specific rotation: $[\alpha]^D$−60.6 (c=0.45, methanol)

Preparation Example 4(c)

dl-Trans-3-imino-1,5-dimethyl-7,7-dichloro-2-azabicyclo[4.1.0]heptane Monohydrochloride

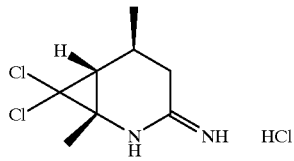

TLC: Rf 0.58 (chloroform:methanol:acetic acid=20:4:1);

NMR (DMSO-$d_6$): δ10.48 (1H, br), 9.56 (1H, br), 9.02 (1H, br), 2.54–2.40 (2H, m), 2.04–1.89 (2H, m), 1.63 (3H, s), 1.26 (3H, d, J=6.4 Hz)

REFERENCE EXAMPLE 8 dl-Trans-3-oxo-5-methyl-7-(2-propenyl)-7-chloro-2-azabicyclo[4.1.0]heptane

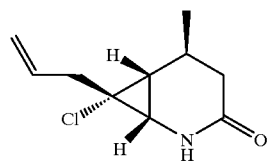

To a solution of 1.26 g of dl-trans-3-oxo-5-methyl-7,7-dichloro-2-(p-methoxybenzyl)-2-azabicyclo[4.1.0]heptane in 13 ml of anhydrous benzene were added 2.58 g of allyltributyltin and 53 mg of 2,2'-azobisisobutyronitrile in an argon atmosphere, and the mixture was heated under reflux for 33 hours. To the reaction mixture were added 2.58 g of allyltributyltin and 53 mg of 2,2'-azobisisobutyronitrile, followed by heating under reflux for 20 hours. After allowing the reaction mixture to cool to room temperature, the reaction mixture was diluted with ethyl acetate and washed with a 5% potassium fluoride aqueous solution. Any insoluble matter produced was separated by Celite filtration. The filtrate was separated into two phases. The aqueous layer was extracted with ethyl acetate, and the extract was combined with the organic layer. The combined organic layer was washed with a saturated sodium chloride aqueous solution, dried over anhydrous magnesium sulfate, followed by filtration. The filtrate was concentrated under reduced pressure, and the residue was purified by silica gel column chromatography to furnish 423 mg of the title compound as a white solid, which had the following physical properties.

TLC: Rf 0.40 (hexane:ethyl acetate=1:5);

NMR (CDCl$_3$): δ6.14 (1H, br), 5.86 (1H, ddt, J=6.6, 10.4, 16.6 Hz), 5.22–5.08 (2H, m), 2.65 (1H, dd, J=1.2, 9.4 Hz), 2.55 (1H, ddt, J=1.2, 6.6, 15.0 Hz), 2.33 (1H, ddt, J=1.2, 6.6, 15.0 Hz), 2.27–2.02 (3H, m), 1.22 (3H, d, J=6.4 Hz), 1.13 (1H, dd, J=4.4, 9.2 Hz)

Preparation Example 5 dl-Trans-3-imino-5-methyl-7-(2-propenyl)-7-chloro-2-azabicyclo[4.1.0]heptane Monohydrochloride

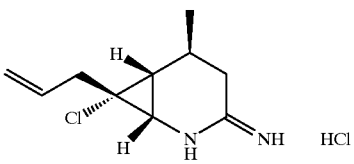

The title compound having the following physical properties was obtained from the compound prepared in Reference Example 8 in the same manner as in Reference Example 4 and Preparation Example 1.

TLC: Rf 0.32 (chloroform:methanol:acetic acid=10:1:1);

NMR (DMSO-$d_6$): δ10.05 (1H, br), 9.34 (1H, br), 8.88 (1H, br), 5.85 (1H, ddt, J=6.6, 10.4, 17.0 Hz), 5.26–5.12 (2H, m), 2.97 (1H, dd, J=1.2, 9.4 Hz), 2.63–2.26 (4H, m), 1.98–1.76 (1H, m), 1.40 (1H, dd, J=5.0, 8.8 Hz), 1.21 (3H, d, J=7.0 Hz)

Preparation Example 5(a)

dl-Trans-3-imino-5-methyl-7-propyl-7-chloro-2-azabicyclo[4.1.0]heptane Monohydrochloride

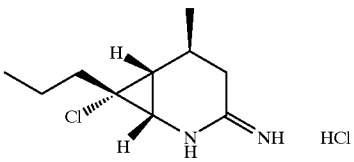

The title compound having the following physical properties was prepared in the same manner as in Reference Example 4 and Preparation Example 1.

TLC: Rf 0.32 (chloroform:methanol:acetic acid=10:1:1);

NMR (DMSO-$d_6$): δ10.05 (1H, br), 9.32 (1H, br), 8.85 (1H, br), 2.89 (1H, dd, J=1.2, 9.0 Hz), 2.47 (1H, dd, J=5.2, 16.0 Hz), 2.33 (1H, dd, J=11.8, 16.0 Hz), 1.96–1.43 (5H, m), 1.34 (1H, dd, J=5.4, 9.0 Hz), 1.21 (3H, d, J=6.8 Hz), 0.91 (3H, t, J=7.2 Hz)

REFERENCE EXAMPLE 9 dl-4-Oxo-3-azabicyclo[4.2.0]octane

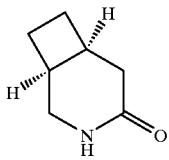

To a solution of 0.48 g of bicyclo[3.2.0]heptan-3-one in 8 ml of formic acid was added 725 mg of hydroxylamine-O-sulfonic acid, followed by heat-refluxing for 3 hours. The reaction mixture was allowed to cool, poured into ice water, neutralized with a 5N sodium hydroxide aqueous solution, and extracted with chloroform. The organic layer was washed, dried, and concentrated under reduced pressure. The residue was purified by silica gel column chromatography to give 48 mg of the title compound as a brown solid, which had the following physical properties.

Shape: dark brown solid;

TLC: 0.46 (chloroform:methanol=9:1);

NMR (CDCl$_3$): δ6.55 (1H, m), 3.39 (1H, ddd, J=2.0 Hz, 4.2 Hz, 13.2 Hz), 3.09 (1H, ddd, J=2.6 Hz, 5.6 Hz, 13.2 Hz), 2.89 (1H, m), 2.70 (1H, m), 2.40 (1H, dd, J=5.8 Hz, 15.4 Hz), 2.32–2.10 (3H, m), 1.90–1.76 (2H, m)

Preparation Example 6 dl-4-Imino-3-azabicyclo[4.2.0]octane Monohydrochloride

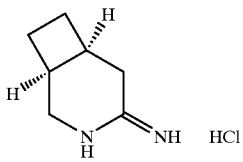

The title compound having the following physical properties was obtained from the compound prepared in Reference Example 9 in the same manner as in Reference Example 4 and Preparation Example 1.

TLC: Rf 0.16 (chloroform:methanol:acetic acid=20:2:1);

NMR (DMSO-d$_6$): δ9.74 (1H, m), 9.20 (1H, m), 8.83 (1H, m), 3.28–3.12 (2H, m), 2.94–2.42 (4H, m), 2.28–2.02 (2H, m), 1.67 (1H, m), 1.46 (1H, m)

REFERENCE EXAMPLE 10

1-(2-Aminoethyl)cyclopropane-1-acetonitrile

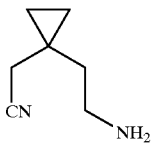

A solution of 5.0 g of cyclopropane-1,1-diacetonitrile in 200 ml of methanol was cooled to −15° C., and 4.95 g of cobalt chloride hexahydrate and 4.15 g of sodium borohydride were added thereto in this order, followed by stirring at that temperature for 15 minutes. The reaction mixture was made acidic by addition of 2N hydrochloric acid and then heated to room temperature, at which the mixture was stirred for 15 minutes, followed by concentration under reduced pressure. Water was added to the residue, and the mixture was extracted with ethyl acetate. The aqueous layer was adjusted to pH 9 with a 5N sodium hydroxide aqueous solution, followed by filtration. Chloroform was added to the filtrate, and the organic layer was washed with a saturated sodium chloride aqueous solution, dried over anhydrous sodium sulfate, and concentrated under reduced pressure. The residue was purified by silica gel column chromatography to give 1.63 g of the title compound, which had the following physical properties.

TLC: Rf 0.17 (chloroform:methanol:acetic acid=10:1:1) Ninhydrin (red violet);

NMR (CDCl$_3$): δ2.85 (2H, t, J=7.6 Hz), 2.41 (2H, s), 1.59 (2H, t, J=7.6 Hz), 0.54 (4H, s)

REFERENCE EXAMPLE 11

2-Ethoxy-3,4,5,6-tetrahydropyridine-4-spiro-cyclopropane Monohydrochloride

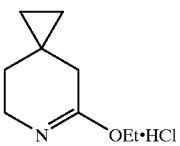

To 830 ml of the compound prepared in Reference Example 10 was added 13 ml of a saturated (about 7N) hydrogen chloride solution in absolute ethanol, followed by stirring at room temperature for 3 hours. The reaction mixture was concentrated to give the title compound having the following physical properties, which was used in the next reaction as unpurified.

TLC: Rf 0.27 (chloroform:methanol:acetic acid=10:1:1) Ninhydrin (brown);

NMR (DMSO-d$_6$): δ12.20 (1H, br; HCl), 4.43 (2H, q, J=7.2 Hz), 3.53 (2H, t, J=5.8 Hz), 2.68 (2H, s), 1.61 (2H, t, J=5.8 Hz), 1.33 (3H, t, J=7.2 Hz), 0.50 (4H, s)

Preparation Example 7

2-Iminopiperidine-4-spiro-cyclopropane Monohydrochloride

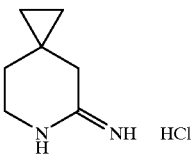

The title compound was prepared from the compound obtained in Reference Example 11 in the same manner as in Preparation Example 1. The physical properties were as follows.

TLC: Rf 0.33 (chloroform:methanol:acetic acid=10:1:1);

NMR (DMSO-d$_6$): δ9.75 (1H, br), 8.78 (1H, br), 8.53 (1H, br), 3.35 (2H; overlapped with water), 2.45 (2H, s), 1.56 (2H, t, J=5.8 Hz), 0.45 (4H, s)

REFERENCE EXAMPLE 12 dl-Trans-4-oxo-6-methyl-3-azabicyclo[4.1.0]heptane

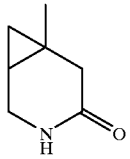

In 81 ml of anhydrous methylene chloride were dissolved 2.0 g of 4,5-didehydro-4-methyl-2-piperidone and 4.35 ml of diiodomethane in an argon atmosphere, and the solution was cooled to 0° C. To the reaction mixture was added 54 ml of a 1 M hexane solution of trimethylaluminum, and the mixture was stirred at room temperature. Two days later, 4.35 ml of diiodomethane was added thereto, and the stirring was continued at room temperature. Three days later, 2.9 ml of diiodomethane and 18 ml of a 1 M hexane solution of trimethylaluminum were added, and the stirring was continued for an additional 1 day period. The reaction mixture was diluted with 60 ml of methylene chloride. After cooling to 0° C., 12.09 g of sodium fluoride and 3.9 ml of water were added thereto, and the mixture was stirred for 30 minutes and filtered. The collected precipitate was dissolved in water and extracted with chloroform. The extract and the filtrate were combined and washed successively with a sodium thiosulfate aqueous solution and a saturated sodium chloride aqueous solution, dried over anhydrous sodium sulfate, and concentrated under reduced pressure. The residue (19.8 g) was purified by column chromatography to obtain 19.8 g of a yellow oil.

The oil was dissolved in 50 ml of methylene chloride and cooled to 0° C. To the solution was added 7.62 g of m-chloroperbenzoic acid (70%), followed by stirring for 2.5 hours. The reaction mixture was diluted with 200 ml of ethyl acetate, a 1N sodium hydroxide aqueous solution was added, and the mixture was stirred. The organic layer was washed successively with a sodium thiosulfate aqueous solution, a sodium hydrogencarbonate aqueous solution, and a saturated sodium chloride aqueous solution, and dried over anhydrous sodium sulfate, followed by concentration under reduced pressure. The residue was purified by column chromatography to give 785 g of the title compound as a colorless oily substance, which had the following physical properties.

Shape: transparent oil;

TLC: Rf 0.53 (chloroform:methanol=10:1);

NMR (CDCl$_3$): δ6.0–5.65 (1H, br), 3.71 (1H, dd, J=12.6, 2.7 Hz), 3.41 (1H, ddd, J=12.6, 5.4, 1.8 Hz), 2.51 (1H, dd, J=33.4, 17.2 Hz), 1.17 (3H, s), 1.00 (1H, m), 0.67 (1H, t, J=5.0 Hz), 0.46–0.38 (1H, m)

Preparation Example 8 dl-Trans-4-imino-6-methyl-3-azabicyclo[4.1.0]heptane Monohydrochloride

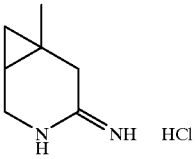

The title compound having the following physical properties was prepared from the compound obtained in Reference Example 12 in the same manner as in Reference Example 4 and Preparation Example 1.

TLC: Rf 0.29 (chloroform:methanol:acetic acid=20:4:1);

NMR (CDCl$_3$): δ9.70–9.50 (1H, br), 9.10–8.90 (1H, br), 8.75–8.50 (1H, br), 3.75–3.50 (2H, m), 3.13 (1H, d, J=17.5 Hz), 2.66 (1H, d, J=17.5 Hz), 1.21 (3H, s), 1.15–1.02 (1H, m), 0.67–0.47 (2H, m)

Formulation Example 1

Tablets

The following components were mixed and tableted in a conventional manner to obtain 100 tablets each containing 100 mg of the active ingredient.

| | |
|---|---|
| (+)-Trans-3-imino-5-methyl-7-chloro-2-azabicyclo[4.1.0]heptane monohydrochloride | 10 g |
| Fibrin calcium glycolate (disintegrant) | 200 mg |
| Magnesium stearate (lubricant) | 100 mg |
| Microcrystalline cellulose | 9.7 g |

Test Examples

Pharmacological Activities of the Compound of the Invention

The pharmacological activity of the compound of formula (I) according to the present invention on i-NOS was examined by the following test.

i-NOS Inhibition Test

To human lung epithelial cell line of A549 were added 10 μg/ml of lipopolysaccharide (LPS), 10 ng/ml of tumor necrosis factor-α (TNF-α), 5 ng/ml of interleukin-1β (IL-1β), and 100 ng/ml of interferon-γ (INF-γ). Sixteen hours later the cells were ruptured by ultrasonication and centrifuged at 54,000 rpm. The supernatant was collected as a source of i-NOS.

i-NOS was made to act on $^{14}$C-labeled L-arginine as a substrate, and L-citrulline produced in the presence of the compound of the invention was determined to calculate the 50% inhibitory concentration of the test compound. More specifically, 10 μl of a 16.8 μM solution of L-[U-$^{14}$C] arginine, 10 μl of the above-prepared i-NOS source, and 10 μl of varied amount of a test compound were added to 70 μl of a solution comprising 50 mM HEPES (N-2-hydroxyethylpiperazine-N'-2-ethanesulfonic acid) (pH 7.8), 1 mM DTT (dithiothreitol), 1 mM NADPH (reduced nicotinamide adenine dinucleotide phosphate), 0.1 mM BH4 (tetrahydrobiopterin), 10 μM FAD (flavin adenine dinucleotide), and 500 units/ml of CaM (calmodulin), and the solution was made to 100 μl. After incubation at 37° C. for 10 minutes, 0.225 ml of a reaction terminating buffer consisting of 100 mM HEPES (pH 5.1 to 5.5) and 10 mM EDTA (ethylenediaminetetraacetic acid) was added while cooling with ice to cease the enzymatic reaction. The reaction solution was passed through a column packed with 0.25 ml of Dowex 50WX-8 (Na⁺ form) to remove unreacted L-arginine and the column was washed with 0.45 ml of the reaction terminating buffer to collect an effluent containing L-citrulline. The radioactivity of the effluent was measured with a liquid scintillation counter, which was taken as NOS activity, from which a 50% inhibition concentration of the test compound was obtained. The results obtained are shown in Table 1.

TABLE 1

| Preparation Example No. | IC$_{50}$ on i-NOS ($\mu$M) |
| --- | --- |
| 1 | 0.22 |
| 2 (g) | 0.092 |
| 3 | 0.012 |
| 3 (a) | 0.090 |
| 3 (c) | 0.020 |
| 3 (f) | 0.18 |
| 3 (g) | 0.047 |
| 3 (i) | 0.13 |
| 4 | 0.021 |
| 4 (a) | 0.057 |
| 7 | 0.20 |

Toxicity

The compounds of the present invention were proved to have sufficiently low toxicity and therefore sufficiently safe for use as pharmaceuticals.

While the invention has been described in detail and with reference to specific embodiments thereof, it will be apparent to one skilled in the art that various changes and modifications can be made therein without departing from the spirit and scope thereof.

This application is based on Japanese application Nos. Hei 9-91830 and Hei 9-273196, the entire contents of which are incorporated hereinto by reference.

What is claimed is:

1. A method of inhibiting inducible nitric oxide synthase in a patient, comprising administering to the patient suffering from a disease induced by inducible nitric oxide synthase, a nitric oxide synthase inhibiting amount of a compound represented by formula (I'):

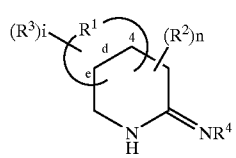

(I')

wherein

—R¹— represents a 3-membered carbocyclic ring together with the carbon atom or atoms to which it is bonded, the carbocyclic ring being condensed to side d or e of the piperidine ring;

R² represents a C$_{1-6}$ alkyl group;

R³ represents a C$_{1-6}$ alkyl group, a C$_{2-6}$ alkenyl group, a C$_{2-6}$ alkynyl group or a halogen atom;

R⁴ represents a hydrogen atom, an amino-C$_{1-4}$ alkyl group or a carbocyclic ring-C$_{1-4}$ alkyl group, which may be substituted with an amino-C$_{1-4}$ alkyl group;

i represents an integer of 0 to 3;

n represents an integer of 0 to 3; and the plural R²'s or R³'s are the same or different, or a non-toxic salt thereof or a hydrate thereof, and wherein the disease is septicemia, endotoxic shock, myocarditis, multiple organ failure, systemic inflammatory response syndrome, shock, tuberculosis, hypotension, rheumatic inflammation, chronic articular rheumatism, ulcerative colitis, stress-induced peptic ulcer, Crohn's disease, autoimmune diseases, post-transplantation tissue disturbances and graft rejection, disturbances in re-perfusion after ischemia, disseminated intravascular coagulation syndrome (DIC), cerebral ischemic disturbances, arteriosclerosis, pernicious anemia, Fanconi's anemia, sickle-cell anemia, pancreatitis, nephrotic syndrome, glomerulonephritis, insulin dependent diabetes mellitus, alcoholism, Parkinson's disease, chronic leukemia, acute leukemia, tumor, side effects of anticancer agents, pulmonary emphysema, Alzheimer's disease, disseminated sclerosis, aging, muscular dystrophy, influenza, malaria, AIDS, radiation injury, or burn.

2. A method for improving efficiency of in vitro fertilization comprising inhibiting a nitric oxide synthase by administering an effective amount of a compound represented by formula (I'):

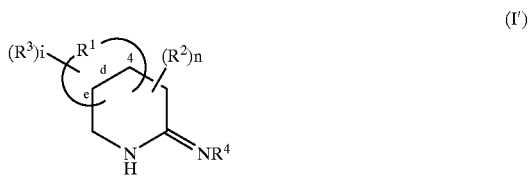

(I')

wherein

—R¹— represents a 3membered carbocyclic ring together with the carbon atom or atoms to which it is bonded, the carbocyclic ring being condensed to side d or e of the piperidine ring;

R² represents a C$_{1-6}$ alkyl group;

R³ represents a C$_{1-6}$ alkyl group, a C$_{2-6}$ alkenyl group, a C$_{2-6}$ alkynyl group or a halogen atom;

R⁴ represents a hydrogen atom, an amino-C$_{1-4}$ alkyl group or a carbocyclic ring-C$_{1-4}$ alkyl group, which may be substituted with an amino-C$_{1-4}$ alkyl group;

i represents an integer of 0 to 3;

n represents an integer of 0 to 3; and the plural R²'s or R³'s are the same or different, or an acid addition salt thereof or a hydrate thereof, wherein the nitric oxide synthase is inducible nitric oxide synthase.

* * * * *